United States Patent [19]
Bright et al.

[11] Patent Number: 5,817,857
[45] Date of Patent: Oct. 6, 1998

[54] (4-HYDROXY-ALKYLPHENYL DIPHENYL PHOSPHATE FLAME RERARDANTS

[75] Inventors: Danielle A. Bright, New City; Ronald L. Pirrelli, Mahopac, both of N.Y.

[73] Assignee: Akzo Nobel NV, Arnhem, Netherlands

[21] Appl. No.: 880,095

[22] Filed: Jun. 20, 1997

Related U.S. Application Data

[62] Division of Ser. No. 742,079, Oct. 31, 1996, Pat. No. 5,728,859.
[51] Int. Cl.$^6$ ....................................................... C07F 9/12
[52] U.S. Cl. ................................................................ 558/194
[58] Field of Search ............................... 558/194; 524/141

[56] References Cited

PUBLICATIONS

Database CAPLUS on STN®, Chemical Abstracts Service, (Columbus, Ohio), Accession No. 1995–869449; Japan Kokai Tokkyo Koho Hei–07–157595, Jun. 20, 1995, abstract, 1995.

*Primary Examiner*—Michael G. Ambrose
*Attorney, Agent, or Firm*—Richard P. Fennelly

[57] ABSTRACT

The present invention is a process for forming monohydroxy-terminated aromatic oligomeric phosphates by the reaction of a diaryl halophosphate, such as diphenyl chlorophosphate, optionally in the presence of some monoaryl dihalophosphate, with an aromatic diol, such as resorcinol, to form the monohydroxy-terminated aromatic oligomeric phosphate. The reaction preferably employs a Lewis acid catalyst, such as magnesium dichloride.

5 Claims, No Drawings

(4-HYDROXY-ALKYLPHENYL DIPHENYL PHOSPHATE FLAME RERARDANTS

This is a division of application Ser. No. 08/742,079, filed Oct. 31, 1996 now U.S. Pat. No. 5,728,859.

BACKGROUND OF THE INVENTION

Aromatic oligomeric phosphate compositions, which are not hydroxy-terminated, are known to persons of ordinary skill in the art with representative examples being described in European Patent Publication Nos. 509,506 and 521,628 and Japanese Patent Publication Nos. 227,632/1988 and 100,785/1994.

Japanese Patent Publication No. 290,086/1993 describes the use as flame retardants for thermoplastic resins of certain monophosphate compounds of the formula $(R^1O)_nP(O)(OR^2OH)_{3-n}$, where n can be 0 to 2, $R^1$ can be lower alkyl, and $R^2$ can be arylene, or diarylene. These flame retardant compounds are prepared from phenol, resorcinol, and phosphorus oxytrichloride as reagents.

U.S. Pat. No. 5,278,212 to H. Nishihara et al. describes the use of certain hydroxyphenyl-containing organophosphorus compounds as flow modifiers for thermoplastic resins. It is disclosed at Col. 6, lines 29–34 that the compounds can also be formed by the reaction of phosphorus oxytrichloride, an aromatic hydroxyl compound, and aromatic dihydroxy compound in the presence of aluminum chloride as a catalyst.

U.S. Pat. No. 4,133,846 to J. A. Albright illustrates certain hydroxy-containing phosphates and polyphosphates where the hydroxy moiety is on the bridging group between the phosphate substituents if diphosphates or polyphosphates are made. Example 4, for example, illustrates the preparation of tetrakis-(chloro-ethyl)pentaerythritol diphosphate by reacting bis-(2-chloroethyl)chlorophosphate and pentaerythritol in the presence of magnesium oxide.

U.S. Pat. No. 4,510,101 to C.E. Pawloski et al. describes certain halogenated phosphorus hydroxyalkyl and t-alkoxyalkyl esters which must also contain at least one —CH$_2$OH substituent directly on one of the phosphorus atoms in the molecule. These esters are disclosed at Col. 3, line 46 to Col. 4, line 13 as being capable of being formed by reaction of a phosphate with dihydroxy compound in the presence of an alkali metal alkoxide catalyst so that the dihydroxy compound reacts with two of the phosphate compounds. This patent (beginning at Col. 4, line 55) also describes another method in which the initial reaction is between phosphorus trichloride and an alcohol.

A hydroxy-terminated aromatic oligomeric phosphate is depicted as one of the products formed by the processes described in Japanese Patent Publication No. 223,158/1989. The product that is desired is a mixture of 22%–65%, by weight, of areactive, hydroxy-terminated monophosphate ester, 15%–30% of a non-eactive, non-hydroxy-terminated phosphate ester, and 5%–63the hydroxy-terminated oligomeric phosphate ester.

The process used to synthesize the product desired by the patentees of Japanese Patent Publication No. 223,158/1989 relies, for example, upon the reaction of a mixture of phenol and aromatic diol (e.g., resorcinol) with phosphorus oxychloride in the presence of a catalyst (e.g., aluminum chloride).

Recent U.S. Pat. No. 5,508,462 to D. A. Bright et al. shows the synthesis of dihydroxy-containing aromatic oligomeric phosphates by use of a monoaryl dihalophosphate reagent, in an initial reaction step, with an aromatic diol, forming a halo-terminated aromatic oligomeric phosphate intermediate, followed by reaction of that intermediate with aromatic diol to form the final desired product.

SUMMARY OF THE INVENTION

The present invention is a process for forming hydroxy-terminated aromatic oligomeric phosphates by the initial reaction of a reagent composition comprising a diaryl dihalophosphate, such as diphenyl chlorophosphate, with an aromatic diol, such as resorcinol, to form the monohydroxy-terminated aromatic oligomeric phosphate. The initial reaction preferably employs a Lewis acid catalyst, such as magnesium dichloride.

DESCRIPTION OF PREFERRED EMBODIMENTS

The process for forming the monohydroxy-terminated aromatic oligomeric phosphates comprises the reaction of a diaryl halophosphate, optionally in the presence of some (for example, up to about 10%, by weight, of the halophosphate-containing reagent mixture, of a monoaryl dihalophosphate, with an aromatic diol to form the desired monohydroxy-terminated aromatic oligomeric phosphate.

The diarylhalophosphate is of the formula $(ArO)_2P(O)X$, where Ar stands for substituted or unsubstituted aryl, such as substituted or unsubstituted phenyl, and X stands for halo, such as chloro or bromo. A preferred reagent to use is diphenyl chlorophosphate.

The optional monoarylhalophosphate is of the formula $ArOP(O)X_2$, where Ar and X are as defined hereinbefore.

The aromatic diol reagent is of the formula HOROH, with R being a hydrocarbyl group such as phenyl, diphenyl, 4,4'-isopropylidenediphenyl, and the like. A particularly preferred diol is resorcinol. Others which can be used include hydroquinone, bisphenol A, bisphenol F, bisphenol S, and 4,4-diphenol.

This reaction step is preferably conducted at an elevated temperature of about 50° C. to about 150° C. using an effective amount (about 0.1% to about 0.5%, by weight of the diarylhalophosphate) of a Lewis acid catalyst, such as magnesium dichloride.

The molar ratio of diarylhalophosphate to diol can be adjusted so as to produce a product having the required amount of hydroxyterminated phosphate. In general, in order to increase the amount of hydroxy-terminated product, a lower ratio of diarylhalophosphate to diol is employed. For example, a 1:1 molar ratio (Example 1) will yield a product having a content of 42% of the hydroxy-terminated species whereas a molar ratio of 1.3:1 (Example 7) will have a a content of 29.7% of the hydroxy-terminated species.

The reaction is illustrated by the following general formula:

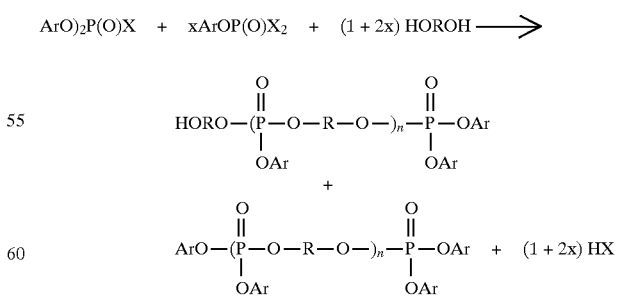

The novel monohydroxy-terminated product from this reaction, which is depicted in the above-described formula, is an aromatic oligomeric phosphate of the following formula:

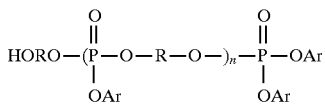

with Ar being defined as earlier described and n ranging from 0 to about 10, for example, from 1 to about 10 in the case of diphosphate and oligomeric phosphate compositions. Mixtures where n is a decimal number are also contemplated.

The product that results from the process described herein, in preferred embodiments, has a low content of triphenyl phosphate, e.g., no more than about 10% by weight, prefereably, no more than about 5% by weight.

The resulting product can be used as a reactive flame retardant for polycarbonate resin compositions, including those of the type described in U.S. Pat. No. 5,618,867. It can also be used as an additive flame retardant in polycarbonate resin compositions.

In accordance with certain preferred embodiments of the present invention a number of novel by-products, which would be useful as flame retardants, were discovered. Depicted below is the generic formula for such compounds, where R is alkyl, preferably straight or branched lower alkyl containing from one to four carbon atoms in the alkyl group:

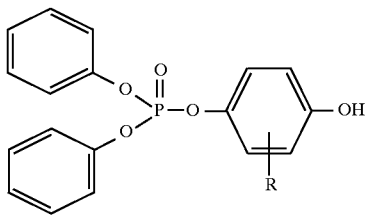

Particularly preferred species include the compounds of the above formula where R is o-methyl, m-methyl, and o-tertbutyl, respectively.

The present invention is further illustrated by the Examples which follow.

EXAMPLE 1

Diphenyl chlorophosphate (134.3 gm, 0.50 mole), resorcinol (55.0 gm, 0.5 mole, and magnesium chloride (500 mg) were heated to 110° C. for four hours, until cessation of hydrogen halide evolution. The reaction mixture was washed with 2×150 ml of water at 40° C. and was dried under vacuum. The product had the following composition by liquid chromatography (LC) resorcinol bis(diphenyl phosphate (49.1%); resorcinol diphenyl phosphate (41.7%); resorcinol (3.7%); and triphenyl phosphate (1.0%).

EXAMPLE 2

The same reaction as described in Example 1 was performed with hydroquinone instead of resorcinol. The reaction mixture solidified upon cooling. LC analysis of the crude reaction mixture showed the following composition: hydroquinone diphenyl phosphate (66%); hydroquinone bis (diphenyl phosphate (25%); hydroquinone (5%); and triphenyl phosphate (0.82%).

EXAMPLE 3

The same process described in Examples 1–2 was carried out using bisphenol A as the diol reagent. The product, which was very viscous, had the following composition: bisphenol A diphenyl phosphate (40.6%); bisphenol A bis (diphenyl phosphate) (29.0%); bisphenol A (9.4%); and triphenyl phosphate (3.7%).

EXAMPLE 4

The same process described in Examples 1–3 was carried out using toluhydroquinone as the diol reagent. The product had the following composition: the two isomers of toluhydroquinone diphenyl phosphate (57.3%); toluhydroquinone bis(diphenylphosphate) (31.2%); toluhydroquinone (5.7%); and triphenyl phosphate (0.95%).

EXAMPLE 5

The same process described in Examples 1–4 was carried out using t-butylhydroquinone as the diol reagent. The product was a solid that was crystallized from methanol and had a purity of 96.6%. Its structure, t-butyl hydroquinyl diphenyl phosphate, was confirmed by proton and $^{13}C$ NMR.

EXAMPLE 6

One hundred grams of a mixture of diphenyl chlorophosphate and monophenyl dichlorophosphate (9:1 weight ratio) was reacted with 44.2 gm (0.402 mole) of resorcinol in the presence of 250 mg of magnesium chloride at 110° C. for six hours. The reaction mixture was washed with 2×125 ml of water at 550° C. After drying, there was left 118.2 gm of a yellow oil (91.2%). LC analysis showed the following composition: resorcinol diphenyl phosphate (37.1%); resorcinol bis(diphenyl phosphate) and higher oligomers (32.9%); hydroxy-terminated resorcinol bis (diphenyl phosphate) (8.4%); resorcinol (5.2%); and triphenyl phosphate (2.9%).

EXAMPLE 7

Fifty grams of a mixture of diphenyl chlorophosphate and monophenyl dichlorophosphate (9:1 weight ratio) was reacted with gm of bisphenol A in the presence of 250 mg of magnesium chloride and 28 ml of heptane at the reflux temperature of heptane for seven hours. After water washing at 600° C. and drying, there was left 86.6 gm (93.8% yield) of a viscous liquid. LC analysis showed the following composition: bisphenol A diphenyl phosphate (40.8%); bisphenol A bis(diphenyl phosphate) and higher oligomers (28.7%); triphenyl phosphate (12.0%); and bisphenol A (2.1%).

EXAMPLE 8

The same general procedure shown in Example 1 was used with the molar ratio of diphenylchlorophosphate being changed from 1:1 to 1.33. The following composition was produced: resorcinol bis(diphenyl phosphate): 66.4%; resorcinol diphenyl phosphate: 29.7%: and triphenyl phosphate: 1.4%.

The foregoing Examples, since they are intended to merely illustrate certain embodiments of the present invention, should not be construed in a limiting sense. the scope of protection sought is set forth in the Claims which follow.

We claim:
1. A compound of the formula
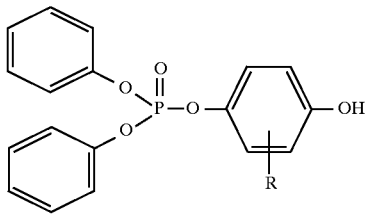
where R is alkyl.
2. A compound as claimed in claim 1 wherein R is lower alkyl of from one to four carbon atoms.
3. A compound as claimed in claim 1 wherein R is o-methyl to the hydroxy group.
4. A compound as claimed in claim 1 wherein R is m-methyl to the hydroxy group.
5. A compound as claimed in claim 1 wherein R is o-tert-butyl to the hydroxy group.
* * * * *